US011484629B2

(12) United States Patent
Chen et al.

(10) Patent No.: US 11,484,629 B2
(45) Date of Patent: Nov. 1, 2022

(54) INTRAVASCULAR DEVICES WITH HIGH TUNGSTEN CONTENT

(71) Applicants: STRYKER CORPORATION, Kalamazoo, MI (US); STRYKER EUROPEAN OPERATIONS LIMITED, Carrigtwohill (IE)

(72) Inventors: Hancun Chen, San Ramon, CA (US); Andrew S. Lee, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 556 days.

(21) Appl. No.: 16/567,845

(22) Filed: Sep. 11, 2019

(65) Prior Publication Data

US 2021/0069386 A1   Mar. 11, 2021

(51) Int. Cl.
*A61F 2/06* (2013.01)
*A61L 31/02* (2006.01)
*A61L 31/14* (2006.01)

(52) U.S. Cl.
CPC ............. *A61L 31/022* (2013.01); *A61L 31/14* (2013.01)

(58) Field of Classification Search
CPC ........................................................ A61F 2/06
See application file for complete search history.

(56) References Cited

U.S. PATENT DOCUMENTS

| | | | |
|---|---|---|---|
| 6,322,576 B1* | 11/2001 | Wallace | A61B 17/12113 606/198 |
| 6,458,119 B1 | 10/2002 | Berenstein et al. | |
| 7,842,054 B2 | 11/2010 | Greene, Jr. et al. | |
| 9,198,670 B2 | 12/2015 | Hewitt et al. | |
| 9,597,155 B2 | 3/2017 | Schewe et al. | |
| 2003/0077200 A1* | 4/2003 | Craig | C22C 38/58 623/1.15 |
| 2004/0193205 A1* | 9/2004 | Burgermeister | A61M 25/0147 606/194 |
| 2005/0065545 A1 | 3/2005 | Wallace | |
| 2007/0067009 A1* | 3/2007 | Gandhi | A61F 2/91 623/1.34 |
| 2007/0162108 A1* | 7/2007 | Carlson | A61M 25/09 623/901 |
| 2015/0283363 A1* | 10/2015 | Hewitt | A61B 17/12118 606/195 |
| 2020/0149137 A1 | 5/2020 | Roth | |

FOREIGN PATENT DOCUMENTS

WO   WO 2004/022122   3/2004

OTHER PUBLICATIONS

PCT International Search Report and Written Opinion for International Appln. No. PCT/US2020/050175, Applicant Stryker Corporation, dated Mar. 19, 2021.
Non-Final Office Action for U.S. Appl. No. 16/872,124 dated Apr. 14, 2022.
PCT Invitation to Pay Additional Fees for International Appln. No. PCT/US2020/050175, Applicant Magic Leap, Inc., dated Dec. 10, 2020 (11 pages).

* cited by examiner

*Primary Examiner* — Cachet I Proctor
(74) *Attorney, Agent, or Firm* — Vista IP Law Group, LLP

(57) ABSTRACT

Implantable medical devices, such as embolic devices and blood flow filters are disclosed, the devices being made at least partially out of a platinum-tungsten alloy, wherein a percentage of tungsten in the alloy is equal to or greater than about 10% of the alloy by weight.

21 Claims, 4 Drawing Sheets

FIG. 1B

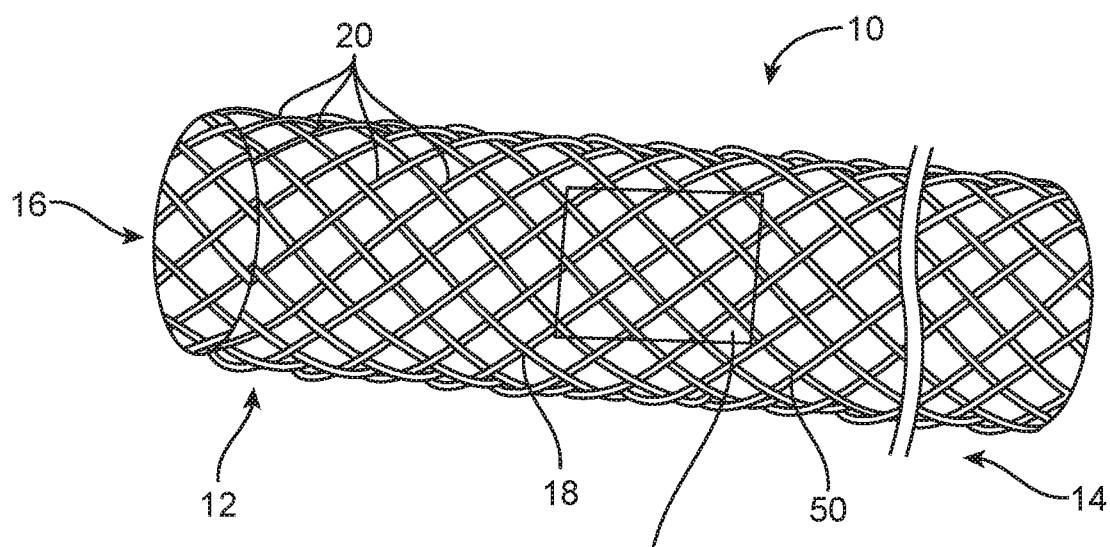
FIG. 1A
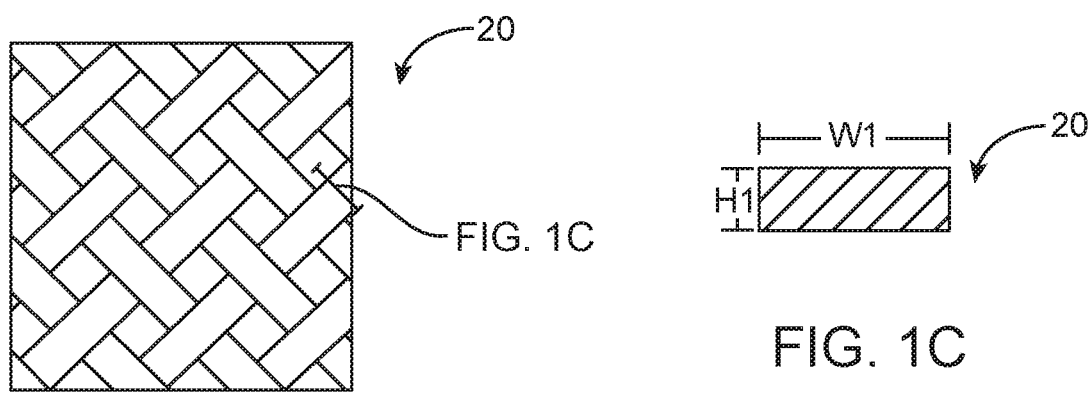
FIG. 1B
FIG. 1C

INTRAVASCULAR DEVICES WITH HIGH TUNGSTEN CONTENT

FIELD

The presently disclosed inventions relate generally to medical devices. More particularly, the present disclosure relates to medical devices, such as intravascular implants, composed of a combination of platinum and tungsten metal alloy.

BACKGROUND

The use of intravascular medical devices has become an effective method for treating many types of vascular disease. Intravascular medical devices such as stents, filters, thromboembolic capture devices, flow diverters, vaso-occlusive devices, collectively referred to herein as "medical devices" are often composed of a variety of biocompatible materials, including polymers (e.g., non-biodegradable and biodegradable plastics) and/or metals. Some of these medical devices are formed by one or more elongate members (e.g., wires, drawn-filled tubes, threads, filaments and the like) that are woven into a braid or mesh pattern. Such braided devices may be utilized for treating various types of vascular defects, such as aneurysms, and may be provided in a wide variety of respective delivery and deployed sizes and shapes; particularly, secondary shapes when the device is deployed in a targeted vasculature site. Some exemplary secondary shapes of braided devices include spherical, ovoid, flat ribbon, helical braided ribbon, or combinations thereof, suitable for the treatment of vascular defects. In general, a suitable intravascular implantable device is inserted into the vascular system of the patient and navigated through the vasculature to a targeted implantation site using known delivery systems and methods.

Medical devices can be made from shape memory or superelastic materials, such as shape memory metals (e.g., shape memory Nitinol) and polymers (e.g., polyurethane). Such shape memory embolic devices can be induced (e.g., by temperature, electrical or magnetic field or light) to take on a shape (e.g., a radially expanded shape) after delivery to a treatment site. Superelastic materials, such as superelastic Nitinol, take on a shape after delivery without the need for an inductive stimulus. Drug delivery medical devices can carry, and/or the surface of the device, can be coated with a bioactive or therapeutic agent (e.g., thrombosis inducing agent).

Various physical attributes of the medical devices can contribute directly to the success rate of the device. These physical attributes include radiopacity, hoop strength, radial force, column strength, flexibility and dimensions of the material used to form the device and the like. Cobalt-chromium (Co—Cr) and stainless steel are commonly used to form stents. These materials are commonly used since such materials having a known history of safety, effectiveness and biocompatibility. These materials however have limited physical performance characteristics as to size, strength, weight, bendability, biostability and radiopacity.

Other commonly used materials include platinum, platinum and tungsten metal alloy, and elgiloy. Known medical devices composed of platinum-tungsten alloy (Pt—W) are illustrated and described (by way of example) in U.S. Pat. Nos. 6,322,576, 6,458,119, 7,842,054, 9,198,670 and 9,597,155, and U.S. Publication No. 20070162108. However, these disclosures are either silent with respect to the specific percentage of platinum and tungsten in the metal alloy or they expressly disclose a preferred or desirable combination of the alloy having platinum (92%) and tungsten (8%) (i.e., Pt-8% wtW).

Due to higher modulus and mechanical strength, some more recent implantable devices including blood flow diversion stents are being made out of Cobalt-chromium (Co—Cr) alloys designed to have suitable radial force. However, the Co—Cr devices have undesirable properties, such as substantially higher magnetic susceptibility of Magnetic Resonance Imaging (MRI) resulting in MR image artifact and poor radiopacity. For the known platinum/tungsten (Pt—W) alloys, up to 8% tungsten (W) has been alloyed to the platinum (Pt) to enhance mechanical strength, handling, and manufacturability. Alloying tungsten (W) greater than 8% is not generally considered because additional tungsten (W) in the platinum (Pt) matrix generally increases its brittleness, compromising the performance of the Pt—W alloy. Although commonly used Pt-8% wtW alloy has relatively low magnetic susceptibility of MRI and higher radiopacity than Co—Cr, the Pt-8% wtW alloy has been found to be not suitable for such flow diversion stents due to the low modulus of the alloy, which results in an undesirably low radial expansion force. In particular, the 8% tungsten (W) was added to the platinum (Pt) alloy to enhance mechanical strength, handling and manufacturability. However, adding more than 8% tungsten (W) has not been explored due to expected increased brittleness of the Pt—W alloy.

SUMMARY

Embodiments of the disclosed inventions are directed to implantable medical devices, such as embolic devices and blood flow filters, that are at least partially made out of (i.e., composed of) a platinum-tungsten alloy in which a percentage of tungsten in the alloy is equal to or greater than about 10% by weight, and preferably in a range of between about 10% to about 20% by weight.

In various embodiments, the implantable devices are made out of one or more elongate members composed of the platinum-tungsten alloy, such as in the form of a cut tube, a coiled wire, or a plurality of wires woven in a braided configuration. Without limitation, the elongate members may include composite wires having at least one layer made out of the platinum-tungsten alloy.

Although it has been traditionally believed in the art of making implantable medical devices that a platinum-tungsten alloy having a percentage of tungsten over 8% is not manufacturable, through experiment, the present inventors discovered that a platinum-tungsten alloy having a percentage of tungsten that is at least 10% by weight could not only be manufactured but would unexpectantly have several advantageous properties. By way of example, and without limitation, such unexpected advantageous properties include having a substantially greater ultimate tensile strength, a substantially greater Young's modulus, and a substantially reduced magnetic susceptibility, respectively, than substantially identically dimensioned alternative materials composed of a platinum-tungsten alloy having a percentage of tungsten that is about 8% by weight.

Other and further aspects and features of embodiments of the herein disclosed inventions will become apparent from the ensuing detailed description in view of the accompanying figures.

BRIEF DESCRIPTION OF THE DRAWINGS

FIGS. 1A-1C are perspective, detailed and cross-sectional views of a braided stent/flow diverter constructed according to embodiments of the disclosed inventions;

DETAILED DESCRIPTION OF THE ILLUSTRATED EMBODIMENTS

Figure 2A:
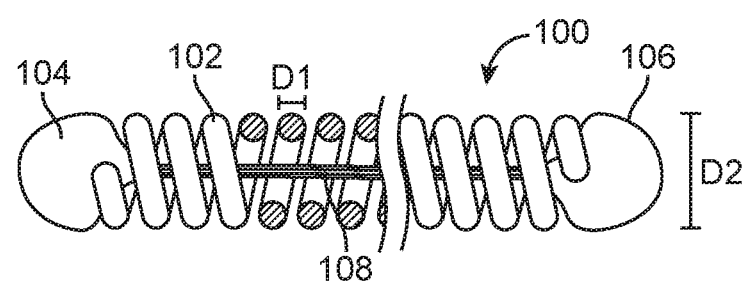
FIGS. 2A-2B are cross-sectional and perspective and view of an embolic coil constructed according to embodiments of the disclosed inventions.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the disclosed inventions, or as a limitation on the scope thereof, which is defined only by the appended claims and their equivalents.

In addition, the respective illustrated embodiments of the disclosed inventions need not have all of the depicted features, and a feature, aspect or advantage described in conjunction with a particular embodiment is not necessarily limited to that embodiment, but can be practiced in other embodiments, even if not so illustrated.

Metal Alloy

In various embodiments of the disclosed inventions, a metal alloy comprising platinum and tungsten (Pt—W) having a percentage (i.e., hereafter mass or weight percentage) of tungsten (W) that is equal or larger than 10% of the alloy, is used in the manufacturing of medical devices. In some embodiments, the percentage of tungsten (W) ranges from 10% to 20% of the alloy. In those embodiments the remaining percentage of the alloy is composed mostly of platinum (Pt), such as for example, where the percentage of platinum (Pt) is equal or less than 90% of the alloy when the percentage of tungsten (W) that is equal or larger than 10%, or where the percentage of platinum (Pt) is equal or less than 80% of the alloy when the percentage of tungsten (W) that is equal or larger than 20%.

In the embodiments of disclosed inventions, the percentage of tungsten (W) is equal or larger than 10% of the platinum/tungsten (Pt—W) alloy used to form the medical devices. Having the percentage of tungsten (W) as equal or larger than 10% of the platinum/tungsten (Pt—W) alloy forming the medical devices provides for improved properties compared to known medical devices having 8% or less of tungsten (W) in the platinum/tungsten (Pt—W) alloy.

As noted above, although conventional wisdom has been that it is not advisable to increase the percentage of tungsten in a platinum-tungsten alloy used for constructing implantable medical devices, the present inventors, when considering and studying the Pt—W phase diagram, believed that Pt-high W content alloys may nonetheless be of some value. From theoretical analysis, the inventors expected there might be some improvements in mechanical strength of the resulting alloy. However, experimentation using Pt-16% W alloy demonstrated exceptionally good and unexpected results with respect to improved mechanical properties, increase in radiopacity (which is critical for blood flow diverter devices) and, most surprisingly, a substantial reduction in magnetic susceptibility (little or no change had been expected).

These unexpected properties of the disclosed platinum/tungsten (Pt—W) alloy comprises, one or more of the following exemplary properties, such as: column strength, radial strength, hoop strength, tensile strength, tensile elongation, stress-strain properties, radial force, radiopacity, flexibility, bendability, heat sensitivity, biocompatibility, and the like. Particularly, a medical device composed of a percentage of tungsten (W) that is equal or larger than 10% of the platinum/tungsten (Pt—W) alloy may increase: radiopacity, radial strength, hardness, yield strength and/or ultimate tensile strength of the device; and/or may further improve stress-strain properties of the device, crimping and/or expansion properties, bendability and/or flexibility, overall strength and/or durability of the device, longitudinal lengthening properties, recoil properties, friction coefficient, heat sensitivity properties, biostability and/or biocompatibility properties, and/or enable manufacturing of smaller, thinner and/or lighter weight medical devices. For example, a medical device composed of a percentage of tungsten (W) that is equal or larger than 10% of the platinum/tungsten (Pt—W) alloy, is configured to have a Young's modulus of equal or larger than 30 Ksi. Additionally, or alternatively, medical devices composed of a percentage of tungsten (W) that is equal or larger than 10% of the platinum/tungsten (Pt—W) alloy are configured to have a magnetic susceptibility in the range of 10 ppm to 300 ppm resulting in reduced artifact during MR imaging.

For example, current flow diversion stents composed of cobalt-chromium (Co—Cr) alloys have substantially higher magnetic susceptibility of MRI (i.e., MR artifact) and poor radiopacity. Thus, making MR follow up imaging not suitable for implanted flow diversion stents made of Co—Cr. In some instances, to improve radiopacity of flow diversion stents made of Co—Cr, Pt-8% W alloy wires are blended with CoCr wires. However, flow diversion stents composed of a percentage of tungsten (W) that is equal or larger than 10% of the platinum/tungsten (Pt—W) alloy, allows for a suitable superior radiopacity and radial force due to the high modulus, as compared for example the CoCr alloy. Additionally, flow diversion stents composed of a percentage of tungsten (W) that is equal or larger than 10% of the platinum/tungsten (Pt—W) alloy have substantially low magnetic susceptibility for MR artifact, allowing MR follow up imaging for implanted flow diversion stents.

These one or more improved properties of the medical device composed of a percentage of tungsten (W) that is equal or larger than 10% of the platinum/tungsten (Pt—W) alloy may be achieved without having to increase the volume and/or weight of the device. Further, these improved properties are likely to be obtained when the volume and/or weight of the medical device is reduced as compared to devices that are at least partially formed from known materials, such as stainless steel, cobalt-chromium (Co—Cr), or platinum/tungsten (Pt—W) alloy having equal or less than 8% of tungsten (W).

Moreover, as long as the percentage of tungsten (W) is equal or larger than 10% of the platinum/tungsten (Pt—W) alloy, it should be appreciated that the percentage of platinum (Pt) in the alloy may be less than the 90% to 80% range, such that other materials may be present. In those embodiments, the platinum/tungsten (Pt—W) alloy may comprise smaller percentage (e.g., 5% or less) of other elements. For example, titanium (Ti) in order to obtain a reduced level of radiopacity, or zirconium (Zr), hafnium (Hf), and/or gold (Au) to achieve desirable levels of magnetic susceptibility, or tantalum (Ta), iridium (Ir), rhenium (Re), rhodium (Rh), ruthenium (Ru) and/or molybdenum (Mo) to obtain desirable levels of mechanical properties, including any combination thereof of these elements or any other suitable element.

Further, medical devices composed with the disclosed platinum/tungsten (Pt—W) alloy having a percentage of tungsten (W) that is equal or larger than 10% of the alloy, may include one or more materials that impart desired properties to the device so as to withstand the manufacturing processes that are needed to produce the device. These manufacturing processes include, for example, laser cutting, etching, crimping, annealing, drawing, pilgering, electroplating, electro-polishing, chemical polishing, cleaning, pickling, ion beam deposition or implantation, sputter coating, vacuum deposition, or the like.

By way of non-limiting examples, the disclosed platinum/tungsten (Pt—W) alloy is at least 95% of the medical devices. Further, the disclosed platinum/tungsten (Pt—W) alloy having a percentage of tungsten (W) that is equal or larger than 10% may be used to form devices such as for example: stents (e.g., slotted tube stents and/or braided or woven stents), filters, thromboembolic capture devices, flow diverters, vaso-occlusive devices, intrasaccular aneurysm implants, vascular delivery assemblies, catheters, reinforcement members, guidewires, delivery wires, radiopaque markers and the like.

By way of non-limiting examples, the disclosed platinum/tungsten (Pt—W) alloy having a percentage of tungsten (W) that is equal or larger than 10% of the alloy configured to at least partially forms the medical device. For example, the alloy may form the majority weight percent of the medical device but that may not be required.

By way of example, the embodiment of FIG. 1A-3F depict medical devices constructed with the disclosed platinum/tungsten (Pt—W) alloy having a percentage of tungsten (W) that is equal or larger than 10% of the alloy.

FIGS. 1A-1C illustrate an exemplary braided embolic device in the form of a tubular braided stent and/or flow diverter 10, constructed according to the one embodiment of the disclosed inventions. FIG. 1A shows the braided stent 10 in a radially expanded delivered configuration, having a proximal portion 12, a distal portion 14 and a lumen 16 extending therebetween. The braided stent 10 is formed out of a plurality of elongate members 20 (e.g., wires, drawn-filled tubes, threads, filaments and the like) that are woven together. FIG. 1B is a two-dimensional plan view of a section of a wall 18 of the braided stent 10, showing that the elongate braid members 20 are woven in a standard repeating "one-over, one-under" pattern 50 (detailed of FIG. 1A), which is a common weave pattern used in known braided embolic devices. One or more of the elongated members 20 are composed of the disclosed platinum/tungsten (Pt—W) alloy having a percentage of tungsten (W) that is equal or larger than 10%. The elongated members 20 of FIGS. 1A-1B can include a ribbon-like configuration having substantially rectangular cross-section (FIG. 1C). As further shown in FIG. 1C, the ribbon-like elongated members 20 comprise a width (W1) of 0.004" (0.102 mm) and a height (H1) of 0.002" (0.051 mm). In some embodiments, the ribbon-like elongated members 20 comprises a maximum width of 0.005" (0.127 mm) and a minimum height of 0.0008" (0.0203 mm). In further embodiments where the elongated members 20 have substantially circular cross-section (not-shown), the diameter of the circular cross-section of the elongated members 20 are in the range between 0.0008" (0.0203 mm) to 0.004" (0.102 mm), and preferably, in the range between 0.001" (0.025 mm) to 0.002" (0.051 mm). It should be appreciated that the elongated members 20 may include other cross-sectional configurations.

In the embodiments of FIGS. 1A-1B, the braid pattern 50 or specification of the braid of the stent 10 includes between 36 to 144 elongated members 20; preferably between 48 to 120 elongated members 20. Additionally, the radially expanded delivered configuration of the braided stent 10 have a PPI between 30 to 200; preferably between 50 to 150.

Referring back to the disclosed platinum/tungsten (Pt—W) alloy having a percentage of tungsten (W) that is equal or larger than 10% forming one or more of the elongated members 20, provides the stent 10 with the following properties: a) the stent 10 would achieve higher radial force due to higher material modulus and strength; b) the stent 10 is configured to be manufactured of smaller elongated members 20 and with a greater wire count to achieve better flow diversion effect; c) the stent 10 is configured to have a reduced MR image artifact for follow up imaging procedures due to low magnetic susceptibility, making the stent 10 more suitable for MR imaging and/or the stent 10 is configured to have full radiopacity, and other advantages, previously disclosed. Further, if the radiopacity of the stent 10 is too high for the application, the device can be manufactured using a combination of elongated members 20 composed of the disclosed platinum/tungsten (Pt—W) alloy and another material or alloy with lower radiopacity, or the device can be manufactured using a composite wire that consists of the disclosed platinum/tungsten (Pt—W) alloy as an external layer and another less radiopaque alloy as the core. The above disclosed properties of the stent 10 composed of the disclosed platinum/tungsten (Pt—W) alloy having a percentage of tungsten (W) that is equal or larger than 10% forming one or more of the elongated members 20, are in comparison with stents composed of cobalt-chromium (Co—Cr) alloys or with stents made out of other available materials.

Figure 2B:
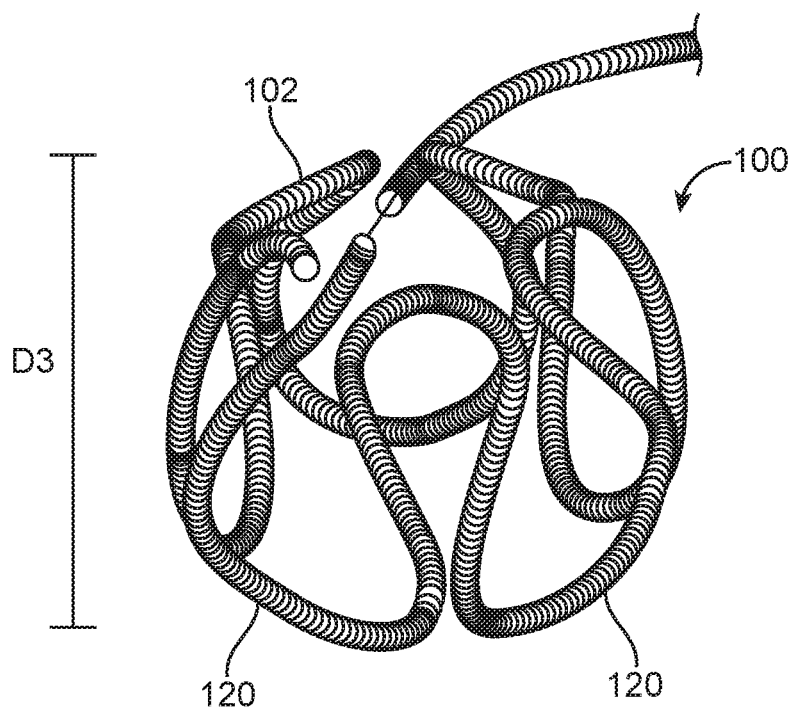

FIGS. 2A-2B illustrate an exemplary intrasaccular device in the form of an embolic coil 100, constructed according to the embodiments of the disclosed inventions. The coil 100 is formed of a helically wound wire 102 having a first end 104 and a second end 106. The coil 100 includes a stretch-resisting member 108 that is fixedly attached both to the first end 104 and to the second end 106. In alternative embodiments, the stretch-resisting member 108 may be attached to one of the two ends or to neither of the two ends. The coil 100 of FIG. 2A is shown in a "primary" winding or shape, and the coil 100 of FIG. 2B is shown in a "secondary" winding or shape. The secondary shape of the coil 100 of FIG. 2B forms a substantially spherical three-dimensional shape having non-overlapping loops 120. It should be appreciated that secondary shape of the coil 100 may assume any other suitable shape. The wire 102 of coil 100 may be formed of a single wire, drawn-filled tubes, threads, filaments or the like. In some embodiments, the wire 102 diameter (D1) ranges from about 0.0005" (0.0127 mm) to about 0.005" (0.127 mm), the primary wind diameter (D2) of the coil 100 ranges from about 0.003" (0.0762 mm) to about 0.030" (0.762 mm) and/or the secondary wind diameter (D3) ranges from about 0.5 mm to about 50 mm, as shown in FIGS. 2A-2B.

The wire 102 of coil 100 (FIGS. 2A-2B) is composed of the disclosed platinum/tungsten (Pt—W) alloy having a percentage of tungsten (W) that is equal or larger than 10%. Where the coil 100 is composed with the disclosed platinum/tungsten (Pt—W) alloy—as, for example compared to coils composed of platinum with 8% tungsten (Pt-8W)—the coil 100 includes the following properties: a) due to the higher modulus resulting in higher column strength the coil 100 is configured to support a longer length without corresponding larger wire 102; b) due to higher yield strength, the coil 100 is configured to be a more effective framing device; c) due to the stability of the alloy, the coil is configured to achieve better shape retention, and deliverability for coils to treat small aneurysms (e.g., under 2 mm due to combination of higher strength and higher modulus).

As previously disclosed, the coil device composed of the disclosed platinum/tungsten (Pt—W) alloy having a percentage of tungsten (W) that is equal or larger than 10% of the wire, has lower MR artifact due to low magnetic susceptibility as compared to the current coils composed of Pt-8% W alloy.

Figure 3A:
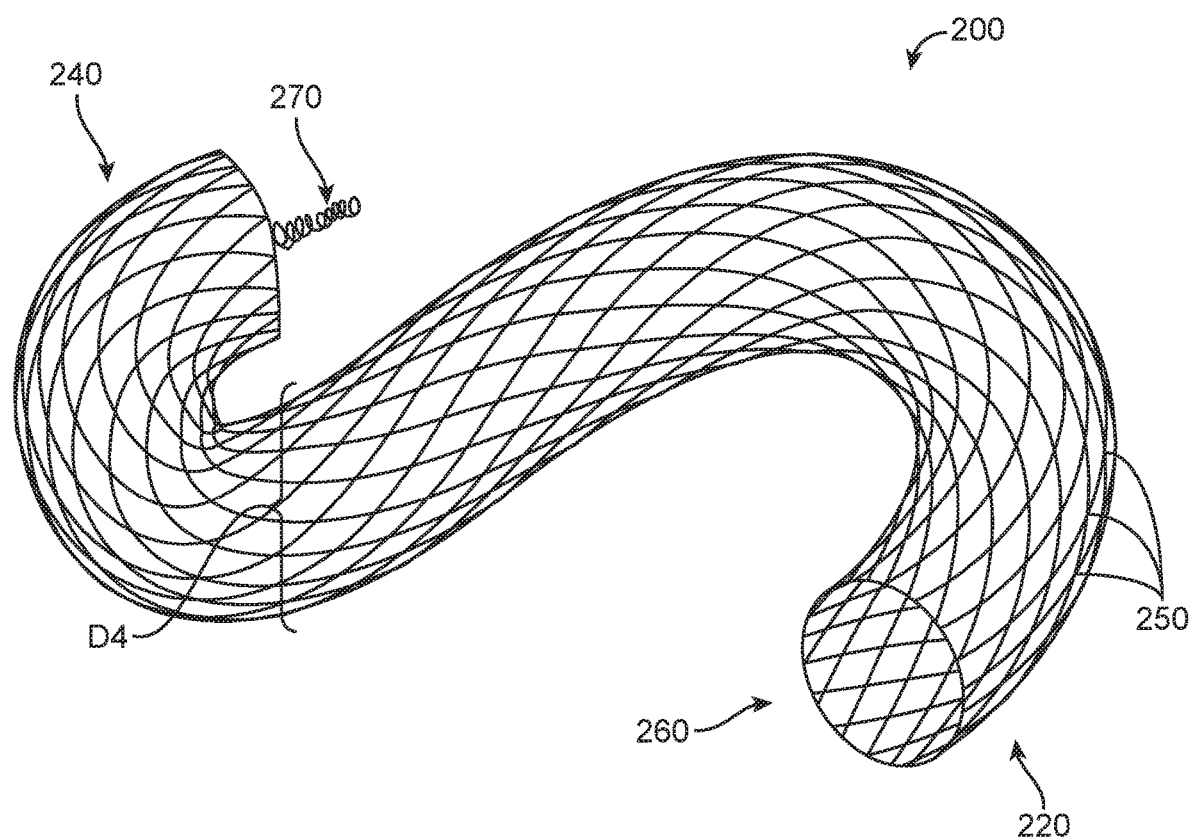
FIGS. 3A-3F are perspective views of an intravascular device constructed according to embodiments of the disclosed inventions.
Figure 3B:
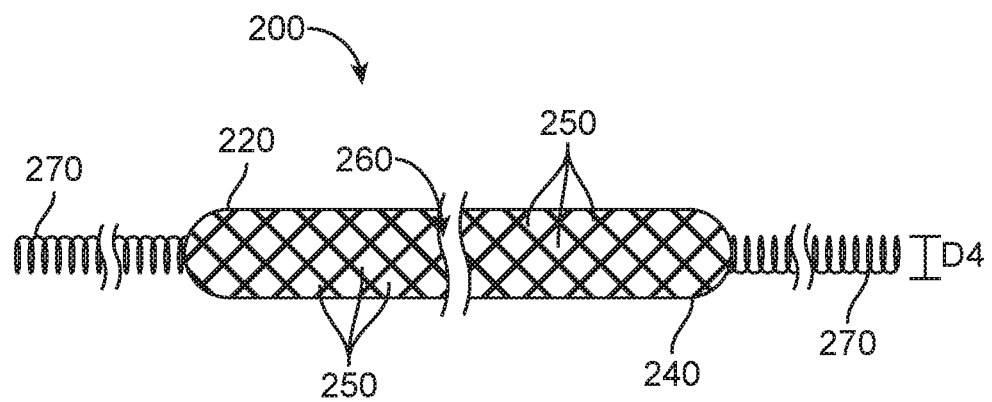
Figure 3C:
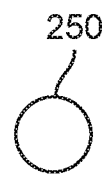
Figure 3D:
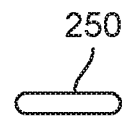
Figure 3E:
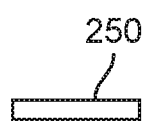
Figure 3F:

FIGS. 3A-3F illustrate an exemplary braided intravascular device having an atraumatic end member, constructed according to the embodiments of the disclosed inventions. FIG. 3A shows the braided intravascular device 200 in a radially expanded (i.e., unconstrained) configuration, having a proximal portion 220, a distal portion 240, and a lumen 260 extending therebetween. The braided intravascular device 200 is formed out of a plurality of elongate members 250 (e.g., wires, drawn-filled tubes, threads, filaments and the like) that are woven (or "braided") together. The braided intravascular device 200 includes an atraumatic member 270 (e.g., coil or the like) at the distal portion 240 of the device 200, as shown in FIG. 3A. It should be appreciated that another atraumatic member 240 may be disposed at the proximal portion 220 of the device 200 (shown in FIG. 3B). The individual elongate members 250 may have substantially circular cross-sections (FIG. 3C), with a cross-sectional diameter in a range of between about 0.0005" (0.0127 mm) to about 0.003" (0.0762 mm). The diameter (D4) of the intravascular device 200 may be in the range of between about 0.01" (0.25 mm) to about 0.2" (5 mm). It should be appreciated that the individual elongate members 250 may have other suitable cross-sections, such as for example, rectangular with rounded corners (FIG. 3D), rectangular with square corners (FIG. 3E), ovoid (FIG. 3F) or the like. The device 200 may also have different, i.e., non-tubular, cross-sectional shapes in their expanded configurations, such as a flattened rectangle with rounded corners (not shown).

One or more of the elongated members 250 and/or the atraumatic member 270 are composed of the disclosed platinum/tungsten (Pt—W) alloy having a percentage of tungsten (W) that is equal or larger than 10% where one or more of the elongated members 250 and/or the atraumatic member 270 are composed with the disclosed platinum/tungsten (Pt—W) alloy, they include the following properties: a) due to the higher modulus resulting in higher column strength the intravascular device 200 includes a better transition between the elongated members 250 and/or the atraumatic member 270; b) the intravascular device 200 may comprise a smaller profile for delivery through smaller internal diameter catheters into a target site of a patient.

Experimental Data

In accordance with the disclosed inventions, experiments were conducted on devices composed of disclosed platinum/tungsten (Pt—W) alloy having a percentage of tungsten (W) that is equal or larger than 10% of the device or portions thereof. A sample wire made of the disclosed platinum/tungsten (Pt—W) alloy (Pt-16% W) and having a diameter of 0.0011" (0.02794 mm) was tested to confirm properties of the disclosed alloy and compared to the commonly used Pt-8% W with same wire diameter of 0.0011". Both wires having an elongation of approximately 2%. The sample wire composed of the disclosed platinum/tungsten (Pt—W) alloy (Pt-16% W) and having a density of 21.08 g/cm3 comprises an ultimate tensile strength (UTS) of 470 Ksi, a Young's modulus of 36 Msi and magnetic susceptibility of 23 ppm. In comparison, the commonly used Pt-8% W wire having a density of 21.26 g/cm3 has an ultimate tensile strength (UTS) of 200-250 Ksi, a Young's modulus of 26 Msi and magnetic susceptibility of 69 ppm.

Therefore, the wire composed of a platinum/tungsten alloy that is approximately 16% tungsten by weight showed approximately a 100% improvement in mechanical strength, approximately a 40% increase in Young's modulus, and approximately a 65% reduction in magnetic susceptibility, respectively, over a substantially identically dimensioned wire composed of a platinum-tungsten alloy that is approximately 8% tungsten by weight. Notably, the disclosed inventions include—without limitation—the various above-described embodiments of implantable medical devices formed out of wires or filaments having the same attributes as the tested wire made from the platinum/tungsten alloy that is approximately 16% tungsten by weight.

Although particular embodiments have been shown and described herein, it will be understood by those skilled in the art that they are not intended to limit the disclosed inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. An implantable medical device, comprising:
   one or more elongate members composed of a platinum-tungsten alloy, wherein the percentage of tungsten in the platinum-tungsten alloy is equal to or greater than about 16% by weight.

2. The device of claim 1, wherein the one or more elongate members comprise a cut tube.

3. The device of claim 1, wherein the one or more elongate members comprise a plurality of composite wires, each having at least one layer composed of the platinum-tungsten alloy.

4. The device of claim 1, wherein the one or more elongate members comprise a plurality of wires or filaments woven in a braided configuration.

5. The device of claim 1, wherein the percentage of tungsten in the platinum-tungsten alloy is a range from about 16% to about 20% by weight.

6. The device of claim 5, wherein the percentage of tungsten in the platinum- tungsten alloy is about 16% by weight.

7. The device of claim 6, wherein the one or more elongate members comprise a wire having an ultimate tensile strength that is approximately 100% greater than an ultimate tensile strength of a substantially identically dimensioned alternative wire composed of an alternative platinum-tungsten alloy having a percentage of tungsten that is about 8% by weight.

8. The device of claim 6, wherein the one or more elongate members comprise a wire having a Young's modulus that is approximately 40% greater than a Young's modulus of a substantially identically dimensioned alternative wire composed of an alternative platinum- tungsten alloy having a percentage of tungsten that is about 8% by weight.

9. The device of claim 6, wherein the one or more elongate members comprise a wire having a magnetic susceptibility that is approximately 60% less than a magnetic susceptibility of a substantially identically dimensioned alternative wire composed of an alternative platinum-tungsten alloy having a percentage of tungsten that is about 8% by weight.

10. An implantable medical device, comprising:
a plurality of wires woven in a braided configuration,
wherein at least a subset of wires of the plurality are composed of a platinum-tungsten alloy having a percentage of tungsten in a range from about 16% to about 20% by weight.

11. The device of claim 10, wherein the wires of the subset comprise composite wires, each including at least one layer composed of the platinum-tungsten alloy.

12. The device of claim 10, wherein at least some wires of the subset composed of the platinum-tungsten alloy have non-circular cross-sections.

13. The device of claim 12, wherein the non-circular cross-sections are selected from the group comprising: rectangular with rounded corners, rectangular with square corners, and ovoid.

14. The device of claim 10, wherein the subset of wires composed of the platinum-tungsten alloy have a greater ultimate tensile strength, a greater Young's modulus, and a lesser magnetic susceptibility, respectively, than substantially identically dimensioned alternative wires composed of an alternative platinum-tungsten alloy having a percentage of tungsten that is about 8% by weight.

15. An implantable occlusive device, comprising:
a wire composed of a platinum-tungsten alloy, wherein the percentage of tungsten in the platinum-tungsten alloy is equal to or greater than about 16% by weight, and wherein the wire is wound into an elongate helical coil.

16. The device of claim 15, wherein the helical coil is treated to assume a three-dimensional secondary shape when unconstrained.

17. The device of claim 16, wherein the secondary shape is substantially spherical.

18. The device of claim 16, wherein in the secondary shape, the coil has non-overlapping loops.

19. The device of claim 15, wherein the wire is a drawn-filled tube.

20. The device of claim 15, wherein the wire has a diameter in a range from about 0.0005" (0.0127 mm) to about 0.005" (0.127 mm), and wherein the coil has a primary wind diameter in a range from about 0.003" (0.0762 mm) to about 0.030" (0.762 mm).

21. The device of claim 15, wherein the wire has a greater ultimate tensile strength, a greater Young's modulus, and a lesser magnetic susceptibility, respectively, than substantially identically dimensioned alternative wire wound into a coil and composed of an alternative platinum-tungsten alloy having a percentage of tungsten that is about 8% by weight.

* * * * *